United States Patent
Marcuccio et al.

(10) Patent No.: US 6,794,529 B2
(45) Date of Patent: Sep. 21, 2004

(54) SUBSTITUTED DIBORON COMPOUNDS

(75) Inventors: Sebastian Mario Marcuccio, Endeavor Hills (AU); Helmut Weigold, Mount Waverley (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 09/899,278

(22) Filed: Jul. 6, 2001

(65) Prior Publication Data

US 2003/0032838 A1 Feb. 13, 2003

Related U.S. Application Data

(60) Provisional application No. 60/216,628, filed on Jul. 7, 2000.

(51) Int. Cl.$^7$ ............................. C07F 5/04; C07F 5/02
(52) U.S. Cl. ......................... 558/286; 558/290; 562/7; 564/9; 564/10
(58) Field of Search .................... 558/287, 288, 558/286, 290; 562/7; 564/9, 10

(56) References Cited

FOREIGN PATENT DOCUMENTS

| AU | PP1100 | 12/1997 |
|---|---|---|
| AU | PP2026 | 2/1998 |
| WO | 98/45265 | 9/1998 |
| WO | 98/58935 | 12/1998 |
| WO | 99/12940 | 3/1999 |
| WO | WO 99/33845 | 7/1999 |

OTHER PUBLICATIONS

CA:127:34269 abs of Tetrahedron Lett by Ishiyama 38(19) pp 3447–3450 1997.*
CA:124:29284 abs of J Org Chem by Ishiyama et al 60(23) 7508–10 1995.*
CA:73:130582 abs of J Chem Soc C by Bowie (16) pp 2228–2229 1970.*
Inorganic Chemistry vol. 37 pp. 5282–5288 by Norman et al. 1998.*
J Org Chem 62, pp. 6458–6459, (1997), Murata et al., "Novel Palladium (O)–Catalysed Coupling Reaction of Dialkoxyborane with Aryl Halides: Convenient Synthetic Route to Arylboranes".

* cited by examiner

*Primary Examiner*—Jean F. Vollano
(74) *Attorney, Agent, or Firm*—Bacon & Thomas

(57) ABSTRACT

The invention relates to a process for the preparation of an organic boronic acid derivative comprising reacting a penta- or hexa-substituted diboron derivative with an organic compound having a halogen or halogen-like substituent at a coupling position in the presence of a Group VIII metal catalyst, such that a direct carbon to boron bond is formed between said coupling position and a boron-containing residue of the penta- or hexa-substituted diboron derivative.

20 Claims, No Drawings

SUBSTITUTED DIBORON COMPOUNDS

This invention relates to a process for the preparation of organic boronic acid derivatives. This invention also relates to a process for covalently coupling organic compounds, in particular to a process for covalently linking organic compounds via formation of an organic boronic acid derivative and coupling to other organic compounds.

Processes for forming covalent bonds between organic compounds, both inter- and intra-molecular, are of particular importance to the synthetic organic chemist. Many such reactions are known, each requiring its own special reaction conditions, solvents, catalysts, ring activating groups etc. Some known types of coupling reactions include the Grignard reaction, Heck reaction and Suzuki reactions (N. Migaura and A. Suzuki, Chem. Rev. 1995, 95, 2457–2483).

Catalysts of palladium, its complexes and its salts are well recognised for activation of C—H bonds towards coupling reactions. In this regard the Heck reaction of an aryl halide with an aryl or vinyl halide in the presence of palladium derivatives has been the subject of intensive study. However commercial development of the Heck reaction has not progressed as rapidly as could have been expected. Other Group VIII metal catalysts, such as platinum and nickel, have also been used to activate such carbon bonds.

Substituted bi- and tri-aryl compounds are of great interest to the pharmaceutical and agrochemical industries. A great number of these compounds have been found to possess pharmaceutical activity, while others have been found to be useful herbicides. There is also interest from the polymer industry in polymers prepared by the linking together of organic compounds.

Conventional methods for covalently linking aromatic rings, such as by reaction of an appropriate Grignard reagent, involve harsh conditions and are not suitable for aromatic rings with active hydrogen containing substituents. Substituents with active hydrogen atoms also can become involved in unwanted side reactions leading to undesirable products. Such substituents need to be protected prior to reaction. Boronic acid derivatives required for the Suzuki reaction are traditionally synthesized through highly reactive organo metallic intermediates. In view of the severity of the reaction conditions the range of substituents which could be present during the linking reaction was considerably limited, and the range of useful reaction media (solvents) was restricted to those which are generally expensive, difficult to remove and/or toxic.

Other difficulties associated with the known coupling reactions are the high temperatures required and the lack of control of the functionality of the products, leading to complex mixtures which can be difficult to separate.

It has now been found that organic boronic acid derivatives can be prepared by reacting an organic compound having a halogen or halogen-like substituent with a penta- or hexa-substituted diboron derivative. The organic boronic acid derivatives are useful in the preparation of covalently coupled organic compounds.

Accordingly, one aspect of the present invention provides a process for the preparation of an organic boronic acid derivative comprising reacting a penta- or hexa-substituted diboron derivative with an organic compound having a halogen or halogen-like substituent at a coupling position in the presence of a Group VIII metal catalyst, such that direct carbon to boron bond is formed between said coupling position and a boron-containing residue of the penta- or hexa-substituted diboron derivative.

Another aspect of the present invention provides a process for the preparation of an organic boronic acid derivative comprising:

(A) reacting a tetra-substituted diboron derivative with a nucleophile to form a penta- or hexa-substituted diboron derivative; and (B) reacting the penta- or hexa-substituted diboron derivative with an organic compound having a halogen or halogen-like substituent at a coupling position in the presence of a Group VIII metal catalyst such that a direct carbon to boron bond is formed between said coupling position and a boron-containing residue of the penta- or hexa-substituted diboron derivative.

It has also been surprisingly found that the two steps, i.e. formation of the penta or hexa substituted diboron derivatives and the reaction of these derivatives with the organic compound can be performed in a single pot without isolation of the penta or hexa derivatives.

Accordingly, in particularly preferred aspect the invention provides a process for the preparation of an organic boronic acid derivative comprising:

(A) reacting a tetra-substituted diboron derivative with a nucleophile to form a penta or as hexa substituted diboron derivative; and (B) reacting the penta- or hexa-substituted diboron derivative in situ with an organic compound having a halogen or halogen-like substituent at a coupling position in the presence of a Group VIII metal catalyst such that a direct carbon to boron bond is formed between said coupling position and a boron-containing residue of the penta or hexa substituted diboron derivative.

The reaction of the penta- or hexa-substituted diboron derivative with an organic compound having a halogen or halogen-like substituent in a coupling position allows for the formation of organic boronic acid derivatives, with only minor amounts of carbon—carbon coupled product formed. This process conveniently allows for the controlled formation of organic boronic acid derivatives and is therefore useful in controlling the formation of carbon to carbon bonds.

In a further aspect, the present invention provides a process for coupling a first organic compound having at a coupling position a halogen or halogen-like substituent and a second organic compound having at a coupling position a halogen or halogen-like substituent comprising:

(A) preparing an organic boronic acid derivative by reacting a penta- or hexa-substituted diboron derivative with said first organic compound in the presence of a Group VIII metal catalyst such that a direct carbon to boron bond is formed between said coupling position and a boron-containing residue of the penta or hexa substituted diboron derivative; and (B) reacting the organic boronic acid derivative with said second organic compound in the presence of a suitable base and a Group VIII metal catalyst, such that a carbon to carbon bond is formed between the respective coupling positions of the organic compounds.

In a particularly preferred embodiment the three steps, i.e. formation of the penta- or hexa-substituted diboron derivative, the reaction of the derivative with the organic compound to form the organic boronic acid derivative, and the coupling of that derivative with another organic compound are performed in the one pot without isolation of intermediates According to this aspect the invention provides a process for coupling a first organic compound having at a coupling position a halogen or halogen-like substituent and a second organic compound having at a coupling position a halogen or halogen-like substituent comprising:

(A) reacting a tetra-substituted diboron derivative with a nucleophile to form a penta or hexa substituted diboron derivative;
(B) preparing a boronic acid derivative by reacting the penta- or hexa-substituted diboron derivative in situ with said first organic compound in the presence of a Group VIII metal catalyst such that a direct carbon to boron bond is formed between said coupling position and a boron-containing residue of the penta- or hexa-substituted diboron derivative; and
(C) reacting the boronic acid derivative in situ with said second organic compound in the presence of a Group VIII metal catalyst and a suitable base such that a carbon to carbon bond is formed between the respective coupling position of the organic compounds.

Prior to step (C) it is preferable to decompose any unreacted tetra-, penta- or hexa-substituted diboron derivative by adding water and a suitable base.

The base should be such that it is strong enough to break the boron to boron bond of the diboron compounds. The base added is preferably one which is capable of catalysing the coupling reaction of step (C).

The term "coupling position" as used herein refers to a position on an organic compound at which coupling to an organic compound is desired. Each organic compound may have one or more, preferably between 1 and 6, coupling positions.

This process conveniently allows for the preparation of both symmetrical and unsymmetrical products by varying the organic compound which is coupled to the organic boronic acid derivative.

As used herein the term "organic compound having a halogen or halogen-like substituent at a coupling position" refers to any organic compound having a carbon to halogen or carbon to halogen-like substituent bond at a position where coupling to the organic compound is desired. The organic compound may be aliphatic, olefinic, aromatic, polymeric or dendritic or any combination thereof. The organic compound may have one or more, preferably between 1 and 6, halogen or halogen-like substituents at coupling positions.

The terms "aromatic" and "aromatic compound(s)" as used herein refer to any compound which includes or consists of one or more aromatic or pseudoaromatic rings. The rings may be carbocyclic or heterocyclic, and may be mono or polycyclic ring systems. Examples of suitable rings include but are not limited to benzene, biphenyl, terphenyl, quaterphenyl, naphthalene, tetradyronaphthalene, 1-benzylnaphthalene, anthracene, dihydroanthracene, benzanthracene, dibenzanthracene, phenanthracene, perylene, pyridine, 4-phenylpyridine, 3-phenylpyridine, thiophene, benzothiophene, naphthothiophene, thianthrene, furan, pyrene, isobenzofuram, chromene, xanthene, phenoxathiin, pyrrole, imidazole, pyrazole, pyrazine, pyrimidine, pyridazine, indole, indolizine, isoindole, purine, quinoline, isoquinoline, phthalazine, quinoxaline, quinazoline, pteridine, carbazole, carboline, phenanthridine, acridine, phenanthroline, phenazine, isothiazole, isooxazole, phenoxazine and the like, each of which may be optionally substituted. The terms "aromatic" and "aromatic compound (s)" include molecules, and macromolecules, such as polymers, copolymers and dendrimers which include or consist of one or more aromatic or pseudoaromatic rings. The term "pseudoaromatic" refers to a ring system which is not strictly aromatic, but which is stablized by means of delocalization of π electrons and behaves in a similar manner to aromatic rings. Examples of pseudoaromatic rings include but are not limited to furan, thiophene, pyrrole and the like.

As used herein, an "olefinic" and "olefinic compound" as used herein refer to any organic compound-having at least one carbon to carbon double bond which is not part of an aromatic or pseudo aromatic system. The olefinic compounds may be selected from optionally substituted straight chain, branched or cyclic alkenes; and molecules, monomers and macromolecules such as polymers and dendrimers, which include at least one carbon to carbon double bond. Examples of suitable olefinic compounds include but are not limited to ethylene, propylene, but-1-ene, but-2-ene, pent-1-ene, pent-2-ene, cyclopentene, 1-methylpent-2-ene, hex-1-ene, hex-2-ene, hex-3-ene, cyclohexene, hept-1-ene, hept-2-ene, hept-3-ene, oct-1-ene, oct-2-ene, cyclooctene, non-1-ene, non-4-ene, dec-1-ene, dec-3-ene, buta-1,3-diene, penta-1,4-diene, cyclopenta-1,4-diene, hex-1,4, diene, cyclohexa-1,3-diene, cyclohexa-1,4-diene, cyclohepta-1,3-diene, cyclohepta-1,3,5-triene and cycloocta-1,3,5,7-tetraene, each of which may be optionally substituted. Preferably the straight chain branched or cyclic alkene contains between 1 and 20 carbon atoms.

In this specification "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, isocyano, cyano, formyl, carboxyl, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, imino, alkylimine, alkenylimine, alkynylimino, arylimino, benzylimino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy mercapto, alkylthio, benzylthio, acylthio, sulphonamido, sulfanyl, sulfo and phosphorus-containing groups.

The organic compound must include at least one halogen or halogen-like substituent at a coupling position to enable reaction with the penta- or hexa-substituted diboron derivative. Preferred halogen substituents include I, Br and Cl. Cl may also be used although Cl is generally less reactive to substitution by the penta- or hexa-substituted diboron derivative or organic boronic acid derivative. The reactivity of chloro substituted organic compounds can be increased by selection of appropriate ligands on the catalyst. The terms "halogen-like substituent" and "pseudo-halide" refer to any substituent which, if present on an organic compound, may undergo substitution with a penta- or hexa-substituted diboron derivative in the presence of a suitable catalyst to give an organic boronic acid derivative, or if present on an organic compound may undergo substitution with an organic boronic acid derivative to give a coupled product. Examples of halogen-like substituents include triflates and mesylates, diazonium salts, phosphates and those described in Palladium Reagents & Catalysts (Innovations in Organic Synthesis by J. Tsuji, John Wiley & Sons, 1995, ISBN 0-471-95483-7).

The process according to the present invention is especially suitable for coupling organic compounds containing substituents which are reactive with organometallic compounds, such as Grignard reagents or alkyl lithiums, therefore unsuitable for reacting using standard Grignard methodology unless these substituents are first protected. One such class of reactive substituents are the active hydrogen containing substituents. The term "active hydrogen containing substituent" as used herein refers to a substituent which contains a reactive hydrogen atom. Examples of such substituents include but are not limited to hydroxy, amino, imino, acetyleno, carboxy (including carboxylato), carbamoyl, carboximidyl, sulfo, sulfinyl, sulfinimidyl, sulfinohydroximyl, sulfonimidyl, sulfoniimidyl, sulfonohydroximyl, sultamyl, phosphinyl, phosphinimidyl, phosphonyl, dihydroxyphosphanyl, hydroxyphosphanyl, phosphono (including phosphonato), hydrohydroxyphosphoryl, allophanyl, guanidino, hydantoyl, ureido, and ureylene. Of these substituents it is particularly surprising that the reaction can be conducted with hydroxy and amino substituents in view of their high reactivity. Carboxyl, sulfo and the like (i.e. acidic) substituents may require additional base. Other reactive substituents include trimethylsilyl.

In the above definitions, the term "alkyl", used either alone or in compound words such as "alkenyloxyalkyl", "alkylthio", "alkylamino" and "dialkylamino" denotes straight chain, branched or cyclic alkyl, preferably $C_{1-20}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

The term "alkoxy" denotes straight chain or branched alkoxy, preferably $C_{1-20}$ alkoxy. Examples of alkoxy include methoxy, ethoxy, n-propoxy, isopropoxy and the different butoxy isomers.

The term "alkenyl" denotes groups formed from straight chain, branched or cyclic alkenes including ethylenically mono-, di- or poly-unsaturated alkyl or cycloalkyl groups as previously defined, preferably $C_{2-20}$ alkenyl. Examples of alkenyl include vinyl, allyl, 1-methylvinyl, butenyl, isobutenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4, pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

The term "alkynyl" denotes groups formed from straight chain, branched or cyclic alkyne including alkyl and cycloalkyl groups as previously defined which contain a triple bond, w preferably $C_{2-20}$ alkynyl. Examples of alkynyl include ethynyl, 2,3-propynyl and 2,3- or 3,4-butynyl.

The term "acyl" either alone or in compound words such as "acyloxy", "acylthio", "acylamino" or "diacylamino" denotes carbamoyl, aliphatic acyl group and acyl group containing an aromatic ring, which is referred to as aromatic acyl or a heterocyclic ring which is referred to as heterocyclic acyl, preferably $C_{1-20}$ acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl, cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

The terms "heterocyclic", "heterocyclyl" and "heterocycl" as used herein on their own or as part of a group such as "heterocyclicalkenoyl", heterocycloxy" or "haloheterocyclyl" refer to aromatic, pseudo-aromatic and non-aromatic rings or ring systems which contain one or more heteroatoms selected from N, S, O and P and which may be optionally substituted. Preferably the rings or ring systems have 3 to 20 carbon atoms. The rings or ring systems may be selected from those described above in relation to the definition of "aromatic".

The term "aryl" as used herein on its own or as part of a group such as "haloaryl" and "aryloxycarbonyl" refers to aromatic and pseudo-aromatic rings or ring systems composed of carbon atoms, preferably between 3 and 20 carbon atoms. The rings or ring systems may be optionally substituted and may be selected from those described above in relation to the definition of "aromatic".

The term "tetra-substituted diboron derivative" may refer to diboronic acid itself or an ester or other derivative of diboronic acid. Examples of suitable esters and derivatives include those of the formula (RX)$_2$B—B(RX)$_2$ where R is hydrogen, optionally substituted alkyl or optionally substituted aryl or —B(XR)$_2$ represents a cyclic group of formula

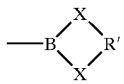

where each X which can be the same or different, can be O, S(O)$_n$ where n is 1 or 2 or NR" where R" is hydrogen or C$_1$–C$_{12}$ alkyl, R' is optionally substituted alkylene, optionally substituted arylene or other divalent group comprising linked aliphatic or aromatic moieties. Preferred tetra-substituted diboron derivatives include bis(pinacolato) diboron (the pinacol ester of -diboronic acid), bis (ethanediolato)diboron, bis(n-propanediolato)diboron and bis(neopentanediolato)diboron. The diboron ester derivatives may be made following the method of Brotherton et al. [R. J. Brotherton, A. L. McCloskey, L. L. Peterson and H. Steinberg, *J. Amer. Chem. Soc.* 82, 6242 (196); R. J. Brotherton, A. L. McCloskey, J. L. Boone and H. M. Manasevit, *J. Amer. Chem. Soc.* 82, 6245 (1960)]. In this process B(NMe$_2$)$_3$, obtained by reaction of BCl$_3$ with NHMe$_2$, is converted to BrB(NMe$_2$)$_2$ by reaction with a stoichiometric amount of BBr$_3$. Reduction in refluxing toluene with sodium metal gives the diboron compound [B(NMe$_2$)$_2$]$_2$ which, after purification by distillation, can be reacted with the alcohol (for example, pinacol) in the presence of a stoichiometric amount of HCl to give the desired ester product. Bis(neopentanediolato)diboron is described by Nguyen et al [Nguyen, P., Lesley, G., Taylor, N. J., Marder, T. B., Pickett, N/L/, Clegg, W., Elsegood, M. R. J., and Norman, N. C., *Inorganic Chem.* 1994, 33,4623-24]. Other suitable "tetra-substituted diboron derivatives" are those analogous to the esters above, but where O is substituted by S(O)$_2$ where n is 1 or 2, or NR" where R" is H or C$_1$–C$_{12}$ alkyl.

The "penta- or hexa-substituted diboron derivative" refers to a diboron derivative having 5 or 6 substituents. It may be a further substituted tetra-substituted diboron derivative, as hereinbefore defined, or an alkali metal salt thereof, wherein one or both of the boron atoms of the tetra-substituted diboron derivative bear a further substituent resulting from reaction between tetra-substituted diboron derivative and a nucleophile. The term "penta- or hexa-substituted diboron derivative" may also collectively refer to a mixture of further penta- or hexa-substituted diboron derivatives resulting from reaction between the tetra-substituted diboron derivative and greater than 1 and less than 2 molar equivalents of nucleophile. It is a further advantageous feature of the present invention that the process can be performed with mixtures of penta- and hexa-substituted diboron derivatives.

Suitable examples of penta- or hexa-substituted diboron derivatives are of general formulae (i) and (ii)

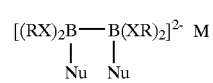 (i)

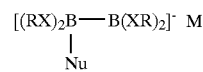 (ii)

wherein M is a counterion and Nu is a nucleophile. Preferably M is a Group I or Group II metal ion. For penta- or hexa-substituted diboron derivatives of formula (i), where M is a monovalent Group I metal ion, each M may be the same or different.

Each Nu may be the same or different and may be a strong nucleophile, such as hydroxide, alkoxide, phenoxide, alkylamino or amino, alternatively the nucleophile may be a complex anion such as that from acacH formed by loss of a proton from an OH, or other anions formed by loss of a proton from OH, CH, SH or NH and may be monodentate or bidentate. It should be able to stabilise the monoboron moiety released in the boron carbon coupling reaction; most preferred Nu are methoxide, ethoxide, n-propoxide, i-propoxide, n-butoxide, t-butoxide, dimethylamino, diethylamino, diisopropylamino, fluoride, cyano or thiolate. Examples of preferred bidentate nucleophiles include those derived from ethylene glycol, ethanolamine or ethylenediamine.

Examples of chiral nucleophiles include those generated from (S)-(−)-1-phenylethanol; (R)-(+)-1-phenylethanol; (−)-1,2:5,6-Di-O-isopropylidene-α-D-glucofuranose; (+)-1,2:5, 6-Di-O-isopropylidene-D-mannitol; (S)-(+)-1,2-O-Isopropylidene-glycerol; (R)-(−)-1,2-O-Isopropylidene-glycerol; (+)-2,3-O-Isopropylidene-L-threitol; (−)-2,3-O-Isopropylidene-D-threitol; (S)-(+)-Methyl 3-hydroxy-2-methylpropionate; (S)-(−)-Methyl lactate; (R)-(−)-Methyl 3-hydroxy-2-methylpropionate; (S)-(+)-1-Amino-2-propanol; (R)-(−)-1-Amino-2-propanol; (+)-2,3-O-Isopropylidene-1,1,4,4-tetraphenyl-D-threitol; and (−)-2,3-L-Isopropylidene-1,1,4,4-tetraphenyl-L-threitol.

Each X, which can be the same or different, can be O, S(O)., where n is 1 or 2 or NR" where R" is hydrogen or C$_1$–C$_{12}$ alkyl, and each R may be the same or different and is independently selected from hydrogen, optionally substituted alkyl, optionally substituted aryl or

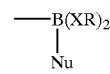

represents a cyclic group of the formula

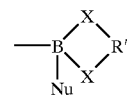

where X, Nu and R' are as previously defined.

The counterion M may be co-ordinated with a compound to further solubilize the base in a particular solvent, for example, crown ethers and cyclams.

The penta- on hexa-substituted diboron derivatives may be chiral compounds, and may have an enantiomeric excess of one or more enantiomers or isomers relative to others. The chirality may be derived from any one or more of the substituents of the penta- or hexa-substituted diboron derivatives. The derivatives may be prepared from a suitable tetra-substituted diboron compound, or the chirality may be introduced using a chiral nucleophile to form the penta- or hexa-substituted diboron derivative. Chiral compounds can be used to advantage to produce chiral products.

Some of these penta- and hexa-substituted diboron derivatives are novel and represent a further aspect of the present invention.

The term "boron-containing residue" as used herein refers to a group of the general formula

wherein X and R are as defined above.

The term "Group VIII metal catalyst" as used herein refers to a catalyst comprising a metal of Group 8 of the periodic table described in CRC Handbook of Chemistry and Physics, 64th edition, 1983-1984, CRC Press. Examples of such metals include Ni, Pt, Pd and Co. Preferably the catalyst is a palladium catalyst as described below, although analogous catalysts of other Group VIII metals may also be used. Examples of suitable Ni catalysts include nickel black, Raney nickel, nickel on carbon and nickel clusters or a nickel complex. Examples of suitable Pt catalysts include platinum black, platinum on carbon and platinum clusters or a platinum complex. The Group VIII metal catalyst may additionally include other metals. Examples of suitable cobalt catalysts include $COCl_2(dppf)$, $CoCl_2(PPh_3)_2$, $CoCl_2[PPh_2(CH_2)_3PPh_2]$, and $CoCl_2[PPh_2(CH_2)_4PPh_2]$.

Examples of suitable palladium catalysts include but are not limited to $Pd_3(dba)_3$, $PdCl_2$, $Pd(OAc)_2$, $PdCl_2(dppf)$ $CH_2Cl_2$, $Pd(PPh_3)_4$ and related catalysts which are complexes of phosphine ligands, (such as $(Ph_2P(CH_2)_nPPh_2)$ where n is 2 to 5, $P(o\text{-tolyl})_3$, $P(i\text{-Pr})_3$, $P(cyclohexyl)_3$, $P(o\text{-MeOPh})_3$, $P(p\text{-MeOPh})_3$, dppp, dppb, TDMPP, TTMPP, TMPP, TMSPP, 2-(di-t-butylphosphino)biphenyl, (R,R)-Me-DUPHOS, (S,S)-Me-DUPHOS, (R)-BINAP, (S)-BINAP, and related water soluble phosphines), related ligands (such as triarylarsine, triarylantimony, triarylbismuth and others as described by W. A. Herrmann and C. K öcher, Angew. Chem. Int. Ed. Engl. 1997, 36, 2162–2187), phosphite ligands (such as $P(OEt)_3$, $P(O\text{-p-tolyl})_3$, $P(O\text{-o-tolyl})_3$, $P(O\text{-iPr})_3$, tris(2,4-di-t-butylphenyl)phosphite and other examples described in the STREM Catalogue No. 18 (Chemicals for Research: metals, inorganics and organometallics 1999–2001)) and other suitable ligands including those containing P and/or N atoms for coordinating to the palladium atoms, (such as for example pyridine, alkyl and aryl substituted pyridines, 2,2'-bipyridyl, alkyl substituted 2,2'-bipyridyl and bulky secondary or tertiary amines), and other simple palladium salts either in the presence or absence of ligands. The palladium catalysts include palladium and palladium complexes supported or tethered on solid supports, such as palladium on carbon, as well as palladium black, palladium clusters, palladium clusters containing other metals, and palladium in porous glass as described in J. Li, A. W-H. Mau and C. R. Strauss, Chemical Communications, 1997, p1275. The same or different palladium catalysts may be used to catalyse different steps in the process. The palladium catalyst may also be selected from those described in U.S. Pat. No. 5,686,608. In certain reactions there are advantages in using ligands with altered basicity and/or steric bulk.

Suitable catalysts also include metallocyclic compounds and compounds that can form metallocyclic species in situ in the reaction medium.

The catalysts according to the present invention may be prepared in situ. For example catalysts consisting of phosphine complexes of palladium can be prepared in situ by addition of a palladium (II) salt such as the acetate and the desired mono- or di-phosphine in a ratio such that the Pd/P atom ratio is approximately 1:2. Arsines, such as for example bis(diphenylarsino) ethane and the like can also be used in conjunction with Pd to make active catalysts for the boronation of aryl halide type species.

The process may be performed in any suitable solvent or solvent mixture provided that it is anhydrous. Examples of such solvents include amides of the lower aliphatic carboxylic acids and lower aliphatic secondary amines, DMSO, aromatic hydrocarbons, nitromethane, acetonitrile, benzonitrile, ethers, polyethers, cyclic ethers, lower aromatic ethers, lower alcohols, and their esters with the lower aliphatic carboxylic acids, pyridine, alkylpyridines, cyclic and the lower secondary and tertiary amines, and mixtures thereof, including mixtures with other solvents. In a preferred embodiment of the invention the process is performed in a protic solvent. Examples of suitable protic solvents include lower alcohols. Most preferably the solvent is ethanol, methanol, isopropanol or mixtures thereof and with other solvents.

The temperature at which each step of the process according to the invention is conducted will depend on a number of factors including the desired rate of reaction, solubility and reactivity of the reactants in the selected solvent, boiling point of the solvent, etc. The temperature of the reaction will generally be in the range of –100 to 250° C. In a preferred embodiment the process is performed at a temperature between 0 and 80°, more preferably between 0 and 40° C.

The terms "nucleophile" and "Nu" as used herein refer to a compound which, when present in the reaction mixture, is capable of nucleophilically reacting with a "tetra-substituted diboron derivative" to form a "penta- or hexa-substituted diboron derivative" as hereinbefore defined. It is also preferable that a nucleophile is chosen which is soluble in the solvent to which it is added. Examples of "nucleophiles" include hydroxides, fluorides, cyanides and thiolates of Li, Na, K, Rb, Cs, ammonium and the group II metals Mg, Ca, & Ba, and their alkoxides and phenoxides, thallium hydroxide, alkylammonium hydroxides and as well as amides such as $LiNMe_2$ and $NaNH_2$. Some of these nucleophiles may be used in conjunction with a phase transfer reagent, such as for example tetraalkylammonium salts or the crown ethers. Nucleophiles that may be used also includes alkali metal salts of potentially chelating ligands, for example acetylacetone.

Examples of "suitable bases" for catalysing the reaction between the organic boronic acid derivative and a further organic compound include the bases listed above as well as caesium carbonate, and potassium carbonate.

As used herein the term "organic boronic acid derivative" refers to the product of the Group VIII metal catalysed reaction between an organic compound having a halogen or halogen-like substituent at a coupling position and a "penta- or hexa-substituted diboron derivative", the product including a carbon to boron bond between the coupling position and a boron-containing residue of the penta- or hexa-diboron derivative. The term includes organic boronic acids, as well as their esters and other derivatives.

Thus, in another aspect of the invention there is provided a process for preparing an organic boronic acid derivative comprising reacting a penta- or hexa-substituted diboron derivative with an organic compound having a halogen or halogen-like substituent and an active hydrogen containing substituent in the presence of a Group VIII metal catalyst.

In a further aspect of the invention, where the organic boronic acid derivative is an ester, there is provided a process for the preparation of an organic boronic acid by the hydrogenolysis or hydrolysis, using established procedures, of the organic boronic acid derivative obtained as hereinbefore described.

The process according to the present invention is applicable to chemistry on solid polymer support or resin bead in the same manner as conventional chemistry is used in combinatorial chemistry and in the preparation of chemical libraries. Thus a suitable organic compound having a halogen or halogen-like substituent at a coupling position which is chemically linked to a polymer surface may be reacted with an organic boronic acid derivative in the presence of a palladium catalyst and a suitable base to form a coupled product linked to the surface of the polymer. Excess reagents and by-products may then be washed away from the surface leaving only the reaction product on the surface. The coupled product may then be isolated by appropriate cleavage of the chemical link from the polymer surface. The process is also possible using the alternative strategy of reacting an organic compound or an organic compound having a halogen or halogen-like substituent linked to a polymer surface with a penta- or hexa-substituted diboron derivative in the presence of a suitable catalyst to form an organic boronic acid derivative chemically linked to the polymer surface. This derivative may then be reacted with an organic compound having a halogen or halogen-like substituent at a coupling position in the presence of a Group III metal catalyst and a suitable base to prepare the coupled product chemically linked to the polymer. Excess reactants and by-products may be removed by suitable washing and the coupled product may be isolated by chemically cleaving the link to the polymer.

In accordance with the present invention it is also possible to directly functionalise the surface of a polymer, e.g. polystyrene, with a halogen, or halogen-like substituent and then convert this functionalised surface to an organic boronic acid derivative surface by reaction of the functionalised polymer with a penta- or hexa-substituted diboron derivative in the presence of a suitable catalyst. The organic boronic acid derivative surface may then be reacted with any suitable organic compound having a halogen or halogen-like substituent. If the organic compound contains other functional groups, for example carboxylic ester, they may be used as linking groups to further extend the chemical reactions applied to the polymer surface.

The term "linking group" as used herein refers to any chain of atoms linking one organic group to another. Examples of linking groups include polymer chains, optionally substituted alkylene group, carboxylic esters and any other suitable divalent group.

It is also possible to prepare polyorganic compounds or other polymers by reaction of organic compounds having more than one halogen or halogen-like substituent. Such organic compounds may be reacted with a penta- or hexa-substituted diboron derivative in the presence of a palladium catalyst to form an organic boronic acid derivative having more than one boron functionality. These derivatives may be reacted with organic compounds or organic compounds having more than one halogen or halogen-like substituent to form a polymer. If the organic compound has three or more halogen or halogen-like substituents which react with the penta- or hexa-substituted diboron derivative then it is possible to prepare dendritic molecules in accordance with the process of the present invention.

The organic compound may be separate molecules or may be linked together such that the organic boronic acid derivative formed after reaction with the penta- or hexa-substituted diboron derivative is able to react at a coupling position located elsewhere in the molecule so as to provide for an intramolecular reaction, such as a ring closure reaction. Similarly the process according to the invention allows intramolecular linking to occur within different organic compounds bearing halogen or halogen-like substituents located at different parts of the molecule. Reaction of one halide substituent with a second penta- or hexa-substituted diboron derivative to form an organic boronic acid derivative allows reaction of that derivative with the halide substituent on the other compound to thereby link the organic compounds.

The process according to the invention is also useful for the preparation of reactive intermediates which are capable of taking part in further reactions or rearrangements. These reactive intermediates may be the organic boronic acid derivative or the coupled products. For example, aryl organic boronic acid derivatives may take part in one or more of the palladium catalysed reactions of aryl boron compounds described by Miyaura and Suzuki in Chem. Rev. 1995, 95 2457–2483.

The present invention allows the formation of organic boronic acid derivatives under exceptionally mild conditions. It is possible to form desired products in good yield at room temperature and below, and with functionalities which may be susceptible to attach by free bases and/or nucleophiles.

The process according to the present invention allow the linking of organic compounds under mild conditions and avoids the use of expensive, difficult to remove and/or toxic reagents and solvents. In this regard boron and boron compounds are generally non-toxic. The reactions may also be performed in relatively cheap solvents such as methanol and ethanol and, in view of the improved control over the reaction steps, it is envisaged that it would be possible to perform the reactions on an industrial scale. The process also allows the linking of organic compounds which contain active hydrogen substituents without the need to protect those substituents during the reaction.

The following examples are provided to illustrate some preferred embodiments of the invention. However it is to be understood that the following description is not to supersede the generality of the invention previously described.

EXAMPLES

A. Effect of Varying the Amount of Base, LiOMe

Example 1

Using one equivalents of alkoxide per diboron species.

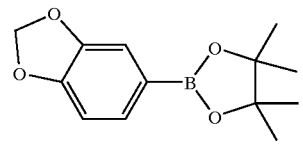

The addition of 1-iodo-3,4-methylenedioxybenzene (1.08 mmol) to a MeOH solution at 20° C. containing equimolar amounts (1 mmol) of bis(pinacolato)diboron and LiOMe and 0.03 mmol $PdCl_2(dppf) \cdot CH_2Cl_2$ led to the formation of the arylboronic acid ester. The reaction was rapid and approx. a 40–45% conversion to product occurred in 45 mins. Very little (approx. 1%) of coupled biaryl product formed, even as the reaction approached completion.

Example 2

Using two equivalents of alkoxide per diboron species.

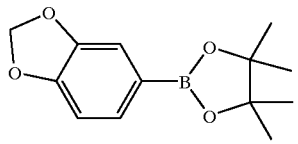

134 mgs (0.53 mmol) of bis(pinacolato)diboron under anaerobic conditions in dry methanol (2 ml) in a reaction tube was reacted with 1.05 ml of a 1 M LiOMe solution in methanol. After stirring, 13 mg (0.016 mmol) of $PdCl_2$(dppf).$CH_2Cl_2$ was added (the solution rapidly darkened) followed by 131 mg (0.53 mmol) of 1-iodo-3,4-methylenedioxybenzene. The reaction was warmed to 30° C. and stirred. On gc analysis after 4.75 hr reaction time, it was found that the reaction was complete and the main product again being the arylboronic acid ester.

The ratio of the ester above to biaryl viz.

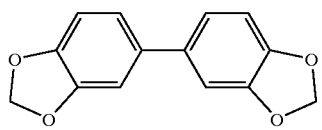

as gauged by gc integration (fid detector) was 97:3. The identity of the species formed was confirmed by gcms.

To the reaction solution was then added 133 mg (0.5 mmol) 2,6-dimethoxy-3-iodopyridine and 350 mg (0.99 mmol) $Cs_2CO_3$ and the reaction stirred overnight (17 h) at 30° C. Gc analysis combined with gcms showed that the arylboronic acid ester had essentially all reacted to form the mixed arylpyridyl species; the gc determined ratio of arylpyridyl species to biaryl was found to be 96:4, indicative of the efficiency of the coupling reaction.

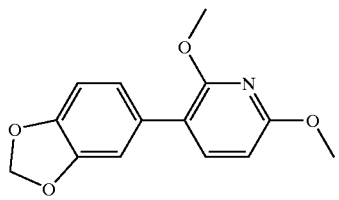

The amount of base required for the formation of arylboronic acid ester in methanol is between one and two mole equivalents based on the diboron compound. For the reaction to go to completion the added base concentration must be at least one equivalent. Reactions in which more than two equivalents of LiOMe were used (viz. four equivalents) still led predominantly to the formation of the arylboronic acid species. Because the reaction is considerably more facile when two equivalents, rather than one, of the base are used, the reaction can be gainfully carried out using just under two equivalents of base without forming significant amounts of symmetrical biaryl side product. A fiber advantage of the above reaction system is that the reaction temperature is low, which reduces possible dehalogenation of the substrate.

Example 3

Reaction using 1.7 equivalents of LiOMe

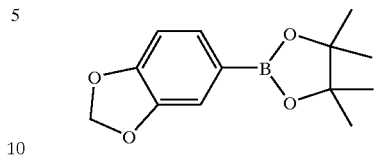

In a Schlenk tube under nitrogen, a solution of 1M LiOMe in MeOH (1.70 ml; 1.70 mmol) was added to a solution of bis(pinacolato)diboron (256 mg; 1.01 mmol) in dry MeOH (4.5 ml) under stirring. After 10 minutes $PdCl_2$(dppf).$CH_2Cl_2$ (23 mg; 0.028 mmol) was added followed by 1-iodo-3,4-methylenedioxybenzene (223 mg; 0.899 mmol). The tube was sealed under nitrogen and stirred at 30° C. for 60 hours. A small amount of the reaction mixture was added to water, extracted into dichloromethane and then dried over $MgSO_4$.

The GC of the reaction solution showed a major peak (92%) identified as the aryl borate by GC/MS and only a trace of dimer (1%).

The reaction solvent was found to affect the reaction. In DMSO at 30° C., using approx. equimolar amounts of bis(pinacolato)diboron and 1-bromo-3,4-methylenedioxybenzene, with $PdCl_2$(dppf).$CH_2Cl_2$ as catalyst, the formation of the arylboronic acid ester was incomplete (approx. 50% yield) when one equivalent of lithium methoxide base (per bis(pinacolato)diboron) was used in the reaction. With two equivalents of lithium methoxide the reaction progressed to completion but the formation of coupled product (biaryl) was significantly larger (in one run it formed to around 50% of the arylboronic acid ester concentration).

B. Effect of Reaction Solvent

Example 4

Reaction in Dioxane

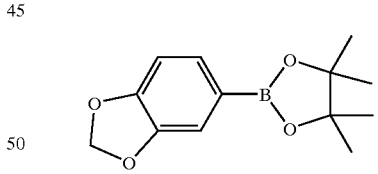

A solution of 1M LiOMe in MeOH (1.70 ml; 1.70 mmol) was taken to dryness under vacuum and placed under nitrogen. Dry dioxane (4 ml) was added followed by bis(pinacolato)diboron (250 mg; 0.984 mmol) and the mixture was stirred at room temperature for 10 minutes. $PdCl_2$(dppf).$CH_2Cl_2$ (24 mg; 0.029 mmol) was added followed by 1-iodo-3,4-methylenedioxybenzene (226 mg; 0.911 mmol). The mixture was then sealed under nitrogen and stirred at 30–35° C. for 18 hours. A small amount of the reaction mixture was added to water, extracted into dichloromethane and then dried over $MgSO_4$. The GC of the reaction solution showed a major peak identified as the aryl borate. Unreacted aryl halide and diboron compound were also present. Only a trace of dimer was formed.

Example 5
Reaction in Ethanol

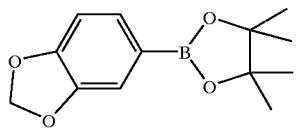

A solution of 1M LiOMe in MeOH (1.70 ml; 1.70 mmol) was taken to dryness under vacuum and placed under nitrogen. Dry EtOH (5 ml) was added followed by bis(pinacolato)diboron (258 mg; 1.02 mmol) and the mixture was stirred at room temperature for 10 minutes. PdCl$_2$(dppf).CH$_2$Cl$_2$ (22 mg; 0.027 mmol) was added followed by 1-iodo-3,4-methylenedioxybenzene (203 mg; 0.818 mmol). The mixture was then sealed under nitrogen and stirred at 40° C. for 18 hours. A small amount of the reaction mixture was added to water, extracted into dichloromethane and then dried over MgSO$_4$. The GC of the reaction solution showed a major peak (74%) identified as the aryl borate by GC/MS. A small amount of dimer (7%) was also formed.

Example 6
Reaction in THF

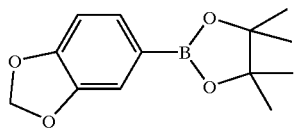

A solution of 1M LiOMe in MeOH (1.70 ml; 1.70 mmol) was taken to dryness under vacuum and placed under nitrogen. Dry THF (5 ml) was added followed by bis(pinacolato)diboron (256 mg; 1.01 mmol) and the mixture was stirred at room temperature for 10 minutes. PdCl$_2$(dppf).CH$_2$Cl$_2$ (25 mg; 0.031 mmol) was added followed by 1-iodo-3,4-methylenedioxybenzene (218 mg; 0.879 mmol). The mixture was then sealed under nitrogen and stirred at 40° C. for 18 hours. A small amount of the reaction mixture was added to water, extracted into dichloromethane and then dried over MgSO$_4$. The GC of the reaction solution showed a major peak identified as the aryl borate by GC/MS. Unreacted aryl halide and diboron compound were also present. Only a trace of dimer was formed.

Example 7
Reaction in i-propanol

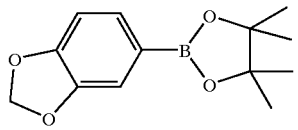

In a Schlenk tube under nitrogen, a solution of 1M LiOMe in MeOH (1.70 ml; 1.70 mmol) was added to a solution of bis(pinacolato)diboron (254 mg; 1.00 mmol) in dry i-PrOH (4 ml) under stirring. After 10 minutes PdCl$_2$(dppf).CH$_2$Cl$_2$ (24 mg; 0.029 mmol) was added followed by 1-iodo-3,4-methylenedioxybenzene (217 mg; 0.875 mmol). The tube was sealed under nitrogen and stirred at 30° C. for 60 hours. A small amount of the reaction mixture was added to water, extracted into dichloromethane and then dried over MgSO$_4$. The GC of the reaction solution showed a major peak (84%) identified as the aryl borate by GC/MS. A small amount of dimer (3%) was formed.

Example 8
Reaction in a Mixed (Methanol/Dioxane) Solvent

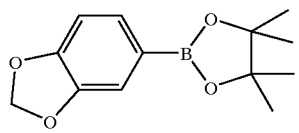

In a Schlenk tube under nitrogen, a solution of 1M LiOMe in MeOH (2.00 ml; 2.00 mmol) was-added to a solution of bis(pinacolato)diboron (290 mg; 1.14 mmol) in dry dioxane (4 ml) under stirring. After 10 minutes PdCl$_2$(dppf).CH$_2$Cl$_2$ (23 mg; 0.028 mmol) was added followed by 1-iodo-3,4-methylenedioxybenzene (224 mg; 0.903 mmol). The tube was sealed under nitrogen and stirred at 30° C. for 18 hours. A small amount of the reaction mixture was added to water, extracted into dichloromethane and then dried over MgSO$_4$. The GC of the reaction solution showed a major peak (83%) identified as the aryl borate by GC/MS. Unreacted aryl halide and diboron compound were also present. Only a trace of dimer (1%) was formed.

C. Reaction with Other Diboron Compounds

Example 9

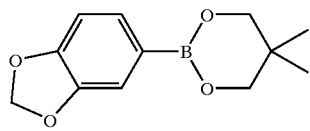

In a Schlenk tube under nitrogen, a solution of 1M LiOMe in MeOH (2.00 ml; 2.00 mmol) was added to a solution of bis(neopentanediolato)diboron (243 mg; 1.08 mmol) in dry MeOH (4.5 ml) under stirring. After 10 minutes PdCl$_2$(dppf).CH$_2$Cl$_2$ (24 mg; 0.029 mmol) was added followed by 1-iodo-3,4-methylenedioxybenzene (235 mg; 0.948 mmol). The tube was sealed under nitrogen and stirred at 30° C. for 18 hours. A small amount of the reaction mixture was added to water, extracted into dichloromethane and then dried over MgSO$_4$. The GC of the reaction solution showed a major peak (86%) identified as the aryl borate by GC/MS. A small amount of dimer (5%) was formed.

Example 10

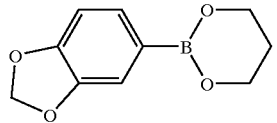

In a Schlenk tube under nitrogen, a solution of 1M LiOMe in MeOH (1.70 ml; 1.70 mmol) was added to a solution of bis(propanediolato)diboron (157 mg; 0.925 mmol) in dry MeOH (4.5 ml) under stirring. After 10 minutes PdCl$_2$(dppf).CH$_2$Cl$_2$ (23 mg; 0.028 mmol) was added followed by 1-iodo-3,4-methylenedioxybenzene (201 mg; 0.810 mmol). The tube was sealed under nitrogen and stirred at 40° C. for 18 hours. A small amount of the reaction mixture was added to water, extracted into dichloromethane and then dried over MgSO$_4$. The GC of the reaction solution showed two major peaks identified as the aryl borate(70%) and the dimer (18%) by GC/MS.

Example 11
A Chiral Arylboronic Acid Ester

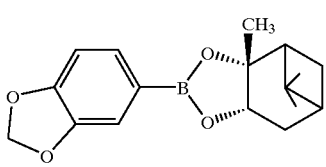

In a Schlenk tube under nitrogen, a solution of 1M LiOMe in MeOH (1.70 ml; 1.70 mmol) was added to a solution of bis((1R,2R,3S,5R)-(−)-pinanediolato)diboron (318 mg; 0.888 mmol) in dry MeOH (4.5 ml) under stirring. After 10 minutes $PdCl_2$(dppf).$CH_2Cl_2$ (23 mg; 0.028 mmol) was added followed by i-iodo-3,4-methylenedioxybenzene (202 mg; 0.814 mmol). The tube was sealed under nitrogen and stirred at 40° C. for 18 hours. A small amount of the reaction mixture was added to water, extracted into dichloromethane and then dried over $MgSO_4$. The GC of the reaction solution showed a major peak identified as the aryl borate by GC/MS.

D. Variation of the Functional Group on the Aromatic Halide

Example 12

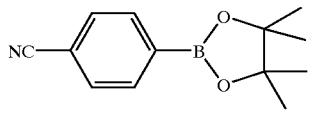

In a Schlenk tube under nitrogen, a solution of 1M LiOMe in MeOH (1.70 ml; 1.70 mmol) was added to a solution of bis(pinacolato)diboron (254 mg; 1.00 mmol) in dry MeOH (4.5 ml) under stirring. After 10 minutes $PdCl_2$(dppf).$CH_2Cl_2$ (25 mg; 0.031 mmol) was added followed by 4-iodobenzonitrile (204 mg; 0.891 mmol). The tube was sealed under nitrogen and stirred at 30° C. for 60 hours. A small amount of the reaction mixture was added to water, extracted into dichloromethane and then dried over $MgSO_4$. The GC of the reaction solution showed a major peak (77%) identified as the aryl borate by GC/MS and only a small amount of dimer (4%).

Example 13

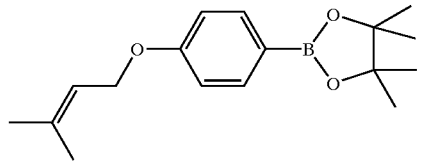

A solution of 1M LiOMe in MeOH (1.70 ml; 1.70 mmol) was taken to dryness under vacuum and placed under nitrogen. Dry DMSO (5 ml) was added followed by bis(pinacolato)diboron (256 mg; 1.01 mmol) and the mixture was stirred at room temperature for 15 minutes. $PdCl_2$(dppf).$CH_2Cl_2$ (26 mg; 0.032 mmol) was added followed by 1-bromo-4-[(3-methylbut-2-enyl)oxy]benzene (218 mg; 0.904 mmol). The mixture was then sealed under nitrogen and stirred at 32° C. for 18 hours. A small amount of the reaction mixture was added to water, extracted into dichloromethane and then dried over $MgSO_4$. The GC and GC/MS of the reaction solution showed the desired aryl borate to be present.

Example 14

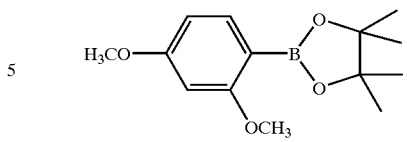

In a Schlenk tube under nitrogen, a solution of 1M LiOMe in MeOH (1.70 ml; 1.70 mmol) was added to a solution of bis(pinacolato)diboron (258 mg; 1.02 mmol) in dry MeOH (4.5 ml) under stirring. After 10 minutes $PdCl_2$(dppf).$CH_2Cl_2$ (22 mg; 0.027 mmol) was added followed by 1-iodo-2,4-dimethoxybenzene (236 mg; 0.894 mmol). The tube was sealed under nitrogen and stirred at 30° C. for 60 hours. A small amount of the reaction mixture was added to water, extracted into dichloromethane and then dried over $MgSO_4$. The GC of the reaction solution showed two major peaks identified as the aryl borate (52%) and dimer (19%) by GC/MS.

Example 15

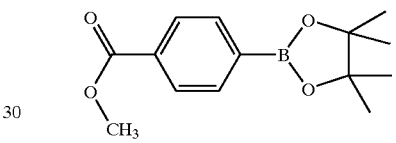

In a Schlenk tube under nitrogen, a solution of 1M LiOMe in MeOH (1.70 ml; 1.70 mmol) was added to a solution of bis(pinacolato)diboron (255 mg; 1.00 mmol) in dry MeOH (4.5 ml) under stirring. After 10 minutes $PdCl_2$(dppf).$CH_2Cl_2$ (22 mg; 0.027 mmol) was added followed by methyl 4-iodobenzoate (235 mg; 0.897 mmol). The tube was sealed under nitrogen and stirred at 30° C. for 60 hours. A small amount of the reaction mixture was added to water, extracted into dichloromethane and then dried over $MgSO_4$. The GC of the reaction solution showed two major peaks identified as the aryl borate and dimer by GC/MS.

Example 16 a)

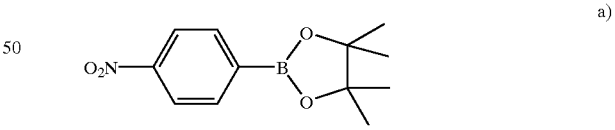

In a Schlenk tube under nitrogen, a solution of 1M LiOMe in MeOH (1.70 ml; 1.70 mmol) was added to a solution of bis(pinacolato)diboron (251 mg; 0.988 mmol) in dry MeOH (4.5 ml) under stirring. After 10 minutes $PdCl_2$(dppf).$CH_2Cl_2$ (23 mg; 0.028 mmol) was added followed by 1-iodo-4-nitrobenzene (224 mg; 0.900 mmol). The tube was sealed under nitrogen and stirred at 25° C. for 60 hours. A small amount of the reaction mixture was added to water, extracted into dichloromethane and then dried over $MgSO_4$. The GC of the reaction solution showed two major peaks identified as the aryl borate and dehalogenated starting material by GC/MS.

b)

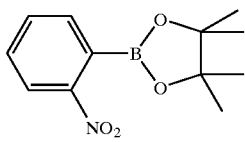

In a Schlenk tube under nitrogen, a solution of 1M LiOMe in MeOH (2 ml; 2 mmol) was added, with stirring, to a solution of bis(pinacolato)diboron (282 mg; 1.11 mmol) in dry MeOH (5 ml). After 10 to 15 minutes the solution was cooled in ice water and PdCl$_2$(dppf).CH$_2$CH$_2$ (25 mg; 0.031 mmol) was added followed by 1-bromo-2-nitrobenzene (203 mg; 1 mmol). The reaction was stired at 0° C. for about 60 hours. A small amount of the reaction mixture was added to water, extracted into dichloromethane and then dried over MgSO$_4$. The GC of the reaction solution showed two major peaks identified as the aryl borate and dehalogenated starting material by GC/MS.

Example 17

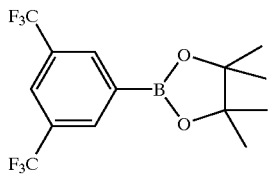

In a Schlenk tube under nitrogen, a solution of 1M LiOMe in MeOH (1.70 ml; 1.70 mmol) was added to a solution of bis(pinacolato)diboron (252 mg; 0.992 mmol) in dry MeOH (4.5 ml) under stirring. After 10 minutes PdCl$_2$(dppf).CH$_2$Cl$_2$ (24 mg; 0.029 mmol) was added followed by 1-iodo-3,5-bis(trifluoromethyl)benzene (305 mg; 0.897 mmol). The tube was sealed under nitrogen and stirred at 20–23° C. for 60 hours. A small amount of the reaction mixture was added to water, extracted into dichloromethane and then dried over MgSO$_4$. The GC of the reaction solution showed a major peak (93%) identified as the aryl borate by GC/MS.

Example 18

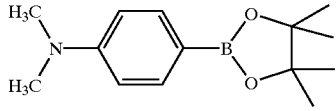

In a Schlenk tube under nitrogen, a solution of 1M LiOMe in MeOH (1.70 ml; 1.70 mmol) was added to a solution of bis(pinacolato)diboron (257 mg; 1.01 mmol) in dry MeOH (5 ml) under stirring. After 10 minutes PdCl$_2$(dppf).CH$_2$Cl$_2$ (22 mg; 0.027 mmol) was added followed by 4-bromo-N,N-dimethylamine (183 mg; 0.915 mmol). The tube was sealed under nitrogen and stirred at 30 CC for 18 hours. A small amount of the reaction mixture was added to water, extracted into dichloromethane and then dried over MgSO$_4$. The GC of the reaction solution showed two major peaks identified as the aryl borate and aryl halide by GC/MS. Only a small amount of dimer was formed.

Example 19

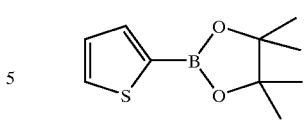

In a Schlenk tube under nitrogen, a solution of 1M LiOMe in MeOH (1.70 ml; 1.70 mmol) was added to a solution of bis(pinacolato)diboron (255 mg; 1.00 mmol) in dry MeOH (5 ml) under stirring. After 10 minutes PdCl$_2$(dppf).CH$_2$Cl$_2$ (24 mg; 0.029 mmol) was added followed by 2-iodothiophene (187 mg; 0.890 mmol). The tube was sealed under nitrogen and stirred at 30° C. for 18 hours. A small amount of the reaction mixture was added to water, extracted into dichloromethane and then dried over MgSO$_4$. The GC of the reaction solution showed two major peaks identified as the aryl borate and diboron compound by GC/MS. No dimer was formed.

Example 20

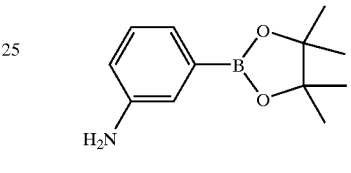

In a Schlenk tube under nitrogen, a solution of 1M LiOMe in MeOH (1.70; 1.70 mmol) was added to a solution of bis(pinacolato)diboron (255 mg; 1.00 mmol) in dry MeOH (5 ml) under stirring. After 10 minutes PdCl$_2$(dppf).CH$_2$Cl$_2$ (23 mg; 0.028 mmol) was added followed by 3-iodoaniline (204 mg; 0.931 mmol). The tube was sealed under nitrogen and stirred at 30° C. for 18 hours. A small amount of the reaction mixture was added to water, extracted into dichloromethane and then dried over MgSO$_4$. The GC of the reaction solution showed a major peak identified as the aryl borate by GC/MS. Only a small amount of dimer was formed.

E. Reaction with Alkenyl Halides

Example 21

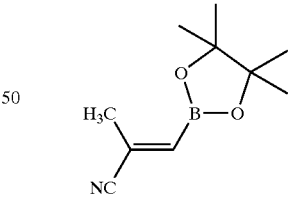

In a Schlenk tube under nitrogen, a solution of 1M LiOMe in MeOH (1.70 ml; 1.70 mmol) was added to a solution of bis(pinacolato)diboron (255 mg; 1.00 mmol) in dry MeOH (5 ml) under stirring. After 10 minutes PdCl$_2$(dppf).CH$_2$Cl$_2$ (24 mg; 0.029 mmol) was added followed by 3-bromo-2-methylacrylonitrile (130 mg; 0.890 mmol). The tube was sealed under nitrogen and stirred at 30° C. for 18 hours. A small amount of the reaction mixture was added to water, extracted into dichloromethane and then dried over MgSO$_4$. The GC of the reaction solution showed three major peaks identified as the vinyl borate, dimer and diboron compound by GC/MS.

Example 22

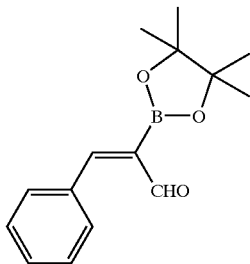

In a Schlenk tube under nitrogen, a solution of 1M LiOMe in MeOH (1.70 ml; 1.70 mmol) was added to a solution of bis(pinacolato)diboron (255 mg; 1.00 mmol) in dry MeOH (5 ml) under stirring. After 10 minutes PdCl$_2$(dppf).CH$_2$Cl, (24 mg; 0.029 mmol) was added followed by α-bromocinnamaldehyde (191 mg; 0.905 mmol). The tube was sealed under nitrogen and stirred at 33° C. for 18 hours. A small amount of the reaction mixture was added to water, extracted into dichloromethane and then dried over MgSO$_4$.

The GC and GC/MS of the reaction solution showed the vinyl borate to have formed.

Example 23

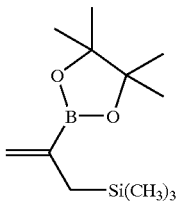

In a Schlenk tube under nitrogen, a solution of 1M LiOMe in MeOH (1.70 ml; 1.70 mmol) was added to a solution of bis(pinacolato)diboron (253 mg; 0.996 mmol) in dry MeOH (5 ml) under stirring. After 10 minutes PdCl$_2$(dppf).CH$_2$Cl$_2$ (22 mg; 0.027 mmol) was added followed by 2-bromoallyltrimethylsilane (177 mg; 0.916 mmol). The tube was sealed under nitrogen and stirred at 33° C. for 18 hours. A small amount of the reaction mixture was added to water, extracted into dichloromethane and then dried over MgSO$_4$. The GC of the reaction solution showed a major peak (66%) identified the vinyl borate by GC/MS. Only a small amount of dimer was formed.

Example 24

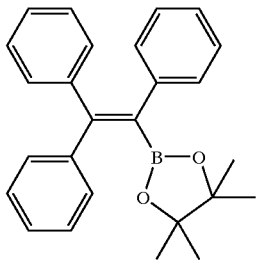

In a Schlenk tube under nitrogen, a solution of 1M LiOMe in MeOH (2.00 ml; 2.00 mmol) was added to a solution of bis(pinacolato)diboron (272 mg; 1.07 mmol) in dry MeOH (4 ml) under stirring. After 10 minutes PdCl$_2$(dppf).CH$_2$Cl$_2$ (23 mg; 0.028 mmol) was added followed by bromotriphenylethylene (325 mg; 0.969 mmol). The tube was sealed under nitrogen and stirred at 30° C. for 18 hours. A small amount of the reaction mixture was added to water, extracted into dichloromethane and then dried over MgSO$_4$. The GC of the reaction solution showed a major peak (88%) identified as the aryl borate by GC/MS. No dimer was formed.

Example 25

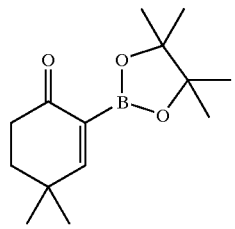

In a Schlenk tube under nitrogen, a solution of 1M LiOMe in MeOH (1.70 ml; 1.70 mmol) was added to a solution of bis(pinacolato)diboron (255 mg; 1.00 mmol) in dry MeOH (4 ml) under stirring. After 10 minutes PdCl$_2$(dppf).CH$_2$Cl$_2$ (24 mg; 0.029 mmol) was added followed by 4,4-dimethyl-2-iodo-2-cyclohexenone (226 mg; 0.904 mmol). The tube was sealed under nitrogen and stirred at 25° C. for 18 hours. A small amount of the reaction mixture was added to water, extracted into dichloromethane and then dried over MgSO$_4$. The GC of the reaction solution showed two major peaks identified as the vinyl borate (22%) and the dimer (36%) by GC/MS.

Example 26

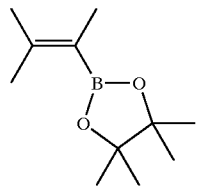

281 mgs (1.10 mmol) of bis(pinacolato)diboron under anaerobic conditions in dry methanol (3 ml) in a reaction tube was treated with 2 ml of a 1 M LiOMe solution in methanol. After stirring for 20 min., 25 mg of PdCl$_2$(dppf).CH$_2$Cl$_2$ was added and the solution darkened rapidly. After 148 mg (1.0 mmol) of 2-bromo-3-methylbut-2-ene was added the reaction solution was warmed to 30° C. and stirred. On gc analysis after 1 hr reaction time, it was found that the required alkenylboronic acid ester had formed in appreciable quantity and at 4 h reaction time was by far the dominant peak in the gc trace. After 24 h reaction time the reaction was essentially completed; the ratio of the peak areas for the required alkenylboronic acid ester: 2-bromo-3-methylbut-2-ene: bis(pinacolato)diboron was determined by gc analysis of the reaction solution, uncorrected for fid response factors, to be 79:3:9. A small amount (3%) of the coupled product 2,3,4,5-tetramethyl-hexa-2,4-diene was formed, all essentially in the first 4 h reaction period.

In DMSO at 30° C., the reaction is slower but again the predominant reaction product is the required alkenylboronic acid ester.

F. Variation of the Phosphine Ligand on the Palladium Catalyst

Example 27

282 mgs (1.11 mmol) of bis(pinacolato)diboron under anaerobic conditions in dry methanol (3 ml) in a reaction tube was treated with 2 ml of a 1 M LiOMe solution in methanol. After stirring, 213 mg (1.06 mmol) of 1-bromo-3,4-methylenedioxybenzene was added followed by 27 mg (0.045 mmol) of $PdCl_2P[Ph_2(CH_2)_4PPh_2]$ and a further 2 ml of methanol. The reaction was warmed to 30° C. and stirred. On gc analysis after 1.5 hr reaction time, it was found that the peak area, uncorrected for response factors (fid detection), of the arylboronic acid ester

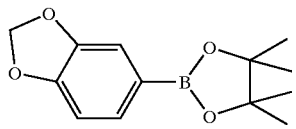

was 20% of the total peak areas. After 18 h reaction at 30° C., the corresponding area increased to above 50%. Dimer formation was not significant, representing only 1.25% of the gc peak areas on analysis of the reaction solution when the reaction was near completion.

Under like conditions (30° C., molar ratio of LiOMe to bis(pinacolato)diboron of ca. 2:1) the catalysts $PdCl_2[Ph_2P(CH_2)_nPPh_2]$, n=2, 5, or 6 and $PdCl_2[(PCy_3)_2]$ where Cy=cyclohexyl, also promoted the formation of the arylboronic acid ester from 1-bromo-3,4-methylenedioxybenzene. The required arylboronic acid ester could also be obtained with catalysts not carrying a phosphine ligand, such as for example, $Pd(CH_3CO_2)_2$. However, with $Pd(CH_3CO_2)_2$ dehalogenation is more pronounced.

When 1-iodo-3,4-methylenedioxybenzene (255 mg, 1.03 mmol) was used instead of 1-bromo-3,4-methylenedioxybenzene in the above reaction at 30° C. [with 2 mmol LiOMe in 2 ml MeOH, 24.6 mg (0.041 mmol) of $PdCl_2[Ph_2P(CH_2)_4PPh_2]$, 284 mg (1.12 mmol) bis(pinacolato)diboron, total reaction volume 7 ml], the reaction was complete when analysed by gc after 17 h reaction time. No iodo compound was found in the products, and the major constituents in the product mix identified by gc/ms were 81% arylboronic acid ester,-2% biaryl, 9% unreacted bis(pinacolato)diboron (excess was used in the reaction) and 4% of the dehalogenated species, 3,4-methylenedioxybenzene.

The higher reactivity of 1-iodo-3,4-methylenedioxybenzene compared to the bromo analogue was also found with other catalysts. For example, with $PdCl_2(dppf).CH_2Cl_2$ (25 mg, 0.031 mmol), 283 mg bis(pinacolato)diboron, 2 mmol LiOMe, reaction volume 7 ml MeOH, the reaction was complete after 4 h with 1-iodo-3,4-methylenedioxybenzene (1.03 mmol) as substrate whereas with 1-bromo-3,4-methylenedioxybenzene (1.03 mmol), arylboronic acid ester formation was estimated to be only about 30% complete.

G. Platinum, Nickel and Cobalt Catalysts

Example 28
Catalysis Using Platinum

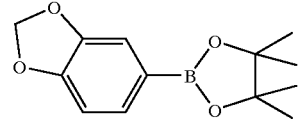

284 mgs (1.12 mmol) of bis(pinacolato)diboron under anaerobic conditions in dry methanol (3 ml) in a reaction tube was treated with 2 ml of a 1 M LiOMe solution in methanol. After stirring, 22 mg (0.028 mmol) of $PtCl_2(PPh_3)_2$ was added followed by 258 mg (1.04 mmol) of 1-iodo-3,4-methylenedioxybenzene and a further 2 ml of methanol. At 60° C. the reaction goes to completion to form the desired product together with 3,4-methylenedioxybenzene. In DMSO the reaction rate is significantly slower than in methanol.

Example 29
Catalysis Using Nickel

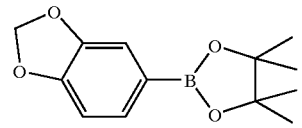

282 mgs (1.11 mmol) of bis(pinacolato)diboron under anaerobic conditions in dry methanol (3 ml) in a reaction tube was treated with 2 ml of a 1 M LiOMe solution in methanol. After stirring, 42 mg (0.17 mmol) of $Ni(CH_3CO_2)_2.4H_2O$ was added followed by 263 mg (1.04 mmol) of 1-iodo-3,4-methylenedioxybenzene. The reaction was warmed to 30° C. and stirred. On gc analysis after 3.5 hr reaction time, it was found that the peak area due to the required arylboronic acid ester was ca. 10% of the total peak areas in the gc. On addition of the nickel catalyst some effervescence occurred in the reaction solution. The low yield of desired product may be due to some catalytic decomposition of bis(pinacolato)diboron. Using $NiCl_2$(dppf) instead of $Ni(CH_3CO_2)_2.4H_2O$, no effervescence was observed and the reaction, at 30° C., although slower than with the corresponding Pd catalyst, yielded over 40% of the required arylboronic acid ester, estimated by gc analysis. No biaryl was observed in the gc of the product, even when the reaction was run at 60° C. The main bi product was 3,4-methylenedioxybenzene.

Example 30
Catalysis Using Cobalt

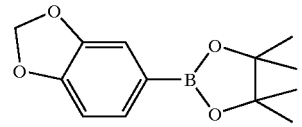

280 mgs (1.10 mmol) of bis(pinacolato)diboron under anaerobic conditions in dry methanol (3 ml) in a reaction tube was treated with 2 ml of a 1 M LiOMe solution in methanol. After stirring, 25 mg of $CoCl_2$(dppf)was added followed by 251 mg (1.01 mmol) of 1-iodo-3,4-methylenedioxybenzene. The reaction was warmed to 60° C.

and stirred. On gc analysis after 16 hr reaction time, it was found that the required arylboronic acid ester had formed together with 3,4-methylenedioxybenzene.

H. Reaction in the Presence of Acetylacetone

Example 31

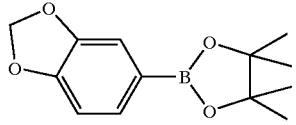

Acetylacetone was converted into the Li compound by reacting a slight excess of acetylacetone with LiOMe in methanol. One equivalent of bis(pinacolato)diboron was then added and the solution stirred at room temp. The solvent was removed and the white powder remaining was used in the reaction.

$PdCl_2(dppf).CH_2Cl_2$ (24.5 mg, 0.03 mmol) and 0.36 g of the product from the reaction of lithium methoxide, acetylacetone and bis(pinacolato)diboron was reacted with 1-iodo-3,4-methylenedioxybenzene (231 mg, 0.93 mmol) in 5 ml methanol. After 1 h at 60° C., the reaction was estimated, by gc, to be ca. 80% complete. The final reaction product distribution, determined after 17.5 h at 60° C., was arylboronic acid ester: biaryl: dehalogenated material is 100:3.6:1.8.

The reaction can also be carried out without attempting the prior isolation of the product from lithium methoxide, acetylacetone and bis(pinacolato)diboron. 0.205 ml acetylacetone was added to a solution of 3 ml methanol and 2 ml 1 m LiOMe in methanol. After ca. 20 mins, 282 mg (1.11 mmol) bis(pinacolato)diboron was added. The clear solution was then treated with 25 mg (0.03 mmol) $PdCl_2(dppf).CH_2Cl_2$. A red solution was formed to which 248 mg (1.0 mmol) 1-iodo-3,4-methylenedioxybenzene was added. The red solution remained clear during warming at 30° C., the colour changing slowly to an orange-to-yellow-brown. Analysis by gc after 22 h indicated that the reaction was complete, giving the required arylboronic acid ester; all the 1-iodo-3,4-methylenedioxybenzene had been consumed. The ratio, based on the gc analysis, of the required arylboronic acid ester: biaryl:3,4-methylenedioxybenzene was 100:1.0:1.5. It was only after the reaction had finished that the colour of the solution darkened noticeably (to a green) and a dark precipitate developed.

In the presence of acetylacetone at 30° C., the Suzuki reaction to give dimer is slow. Reaction of 2 equivalents of 1-iodo-3,4-methylenedioxybenzene with 1 equivalent of bis(pinacolato)diboron and 4 equivalents each of LiOMe and acetylacetone in methanol gave over the first 3 h reaction period essentially no coupled product (gc area ratio of the required arylboronic acid ester:diaryl was 185:1). This ratio slowly increased with reaction time and even after 48 h at 30° C., the above ratio was 2.7:1.

I. Isolation of the Adduct Species Prior to Reaction

Example 32

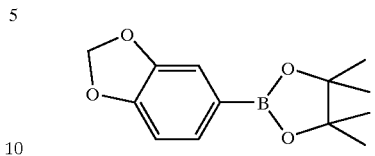

The adduct was prepared by reaction of 2 equivalents of LiOMe in methanol with a solution of bis(pinacolato) diboron in methanol. After stirring for several hr at room temp, the solvent was removed under reduced pressure to give a white powder. $^{11}B$ nmr shows that when bis (pinacolato)diboron reacts with 2 equivalents of LiOMe, the $^{11}B$ resonance moves upfield from 30.9 ppm to 4.67 ppm (external ref.$BF_3$.OEt,; solvent methanol). 300 mgs (0.91 mmol) of bis(pinacolato)diboron/2LiOMe species was reacted in the presence of 25 mg $PdCl_2(dppf).CH_2Cl_2$ with 253 mg (1.02 mmol) 1-iodo-3,4-methylenedioxybenzene under anaerobic conditions in dry methanol (5 ml) in a reaction tube at 30° C. After 2.5 hr reaction time gc analysis of the reaction solution indicated that the peak area of the arylboronic acid ester (uncorrected for response factors) was near 75% of the total peak area. The biaryl peak area was estimated at 2.7%, the remainder unreacted starting materials.

J. Reaction at Elevated Temperatures

Example 33

Reaction at 60° C. Using One Equivalent of LiOMe.

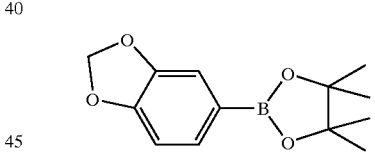

284 mgs (1.12 mmol) of bis(pinacolato)diboron under anaerobic conditions in dry methanol (3 ml) in a reaction tube was treated with 1 ml of a 1 M LiOMe solution in methanol. After stirring, 24 mg (0.029 mmol) of $PdCl_2$(dppf).$CH_2Cl$ was added followed by 251 mg (1.01 mmol) of 1-iodo-3,4-methylenedioxybenzene and a further 2 ml of methanol. Reaction volume=6 ml methanol. The reaction was warmed to 60° C. and stirred. On gc analysis after 3 hr reaction time, it was found that the reaction was complete, no 1-iodo-3,4-methylenedioxybenzene being found in the solution by gc/ms. The bis(pinacolato)diboron (added in excess to the reaction) was not all consumed. The ratio of arylboronic acid ester to biaryl to dehalogenated product was estimated to be 94:3:2 on the basis of the gc peak area ratio.

In neat DMSO the reaction under the above conditions does not yield as much product and dimer formation is more significant.

K. Using Anhydrous KOH as Base

Example 34

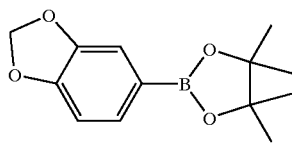

142 mgs (0.56 mmol) of bis(pinacolato)diboron under anaerobic conditions was dissolved in dry methanol (3 ml) in a reaction tube and the treated with 1.0 ml of a 1 M KOH solution in methanol. The reaction solution remained clear and colourless. After stirring, 13.7 mg (0.017 mmol) of $PdCl_2(dppf).CH_2Cl_2$ was added (the solution rapidly darkened) followed by 128 mg (0.64 mmol) of 1-bromo-3,4-methylenedioxybenzene. The reaction was warmed to 30° C. and stirred. On gc analysis after 2 hr reaction time, it was found that the reaction was more than half complete. After 19 hr, all the diboron species bad been consumed. The main product was the arylboronic acid ester. The ratio of arylboronic acid ester to biaryl was greater than 91:9 assuming like fid/gc detection factors. Very little dehalogenated material was observed.

On addition of a further 1.1 ml (1.1 mmol) of KOH solution together with excess m-bromotoluene (0.163 g, 0.95 mmol), and warming to 30° C., the formation of the mixed biaryl compound

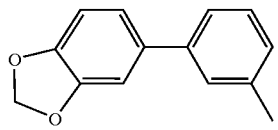

was evident.

The reaction to form the arylboronic acid ester in which only one equivalent of KOH was employed was slower than in the above example where two equivalents of KOH were used.

Example 35
Using Diboronic Acid and KOH.

95 mgs (1.06 mmol) of diboronic acid (white powder) was dissolved under anaerobic conditions in dry methanol (3 ml) in a reaction tube. On addition of 2 ml of a 1 M KOH solution in methanol a precipitate formed that did not redissolve on stirring. After adding 25 mg (0.031 mmol) of $PdCl_2(dppf).CH_2Cl_2$ and 198 mg (0.99 mmol) of 1-bromo-3,4-methylenedioxybenzene, the reaction mixture rapidly darkened to a greenish-brown suspension. The reaction was warmed to 30° C. and stirred for 19 hr. Gc analysis indicated that the reaction was near complete as little bromide compound was evident; a little dimer was also formed. The arylboronic acid formed

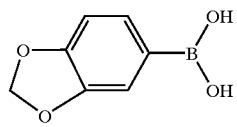

was not observed in the gc analysis, presumably removed by the water wash (3x) of an ether solution of the reaction mixture. However, on addition of fresh catalyst and a further 1.1 ml (1.1 mmol) of KOH solution together with excess m-bromotoluene (0.206 g, 1.15 mmol), and warming to 30° C., the formation of the mixed biaryl compound

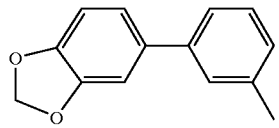

was evident (by gc, gcms).

The use of one equivalent of base was sufficient for reaction to occur to yield the arylboronic acid, but the rate of its formation was slower than when two equivalents of base were employed.

L. Using $B_2[NMe_2]_4$

Example 36

Using $B_2[(NMe_2)_4]$

Added 0.23 ml (1 mmol) of $B_2[(NMe_2)_4]$ into a tube under nitrogen and then added 2.3 ml MeOH followed by 2 ml of 1 M LiOMe in MeOH. On addition of $PdCl_2(dppf).CH_2Cl_2$ (26 mg) the solution rapidly darkened. 1-bromo-3,4-methylenedioxybenzene (0.215 g, 1.07 mmol) was then added and a further 1 ml of MeOH. The solution was warmed to 30° C. After 20 h reaction time no more bromo compound was evident (by gc) in the reaction mixture. The solution was then treated with 268 mg of 2,6-dimethoxy-3-iodopyridine and 409 mg $Cs_2CO_3$. The conversion (at 30° C.) of the reactants to the arylpyridyl

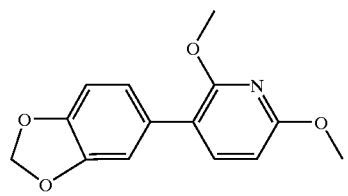

was slow.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. A process for the preparation of an organic boronic acid ester, organic boronic thioester or organic boronic acid amide comprising reacting a penta- or hexa-substituted diboron compound of formula (i) or (ii)

(ii)

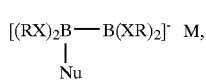

or a mixture of diboron compounds of formula (i) and (ii), wherein M is a counterion and Nu is a nucleophile, and each X, which is the same or different, is O, $S(O)_n$, where n is 1 or 2 or NR" where R" is hydrogen or $C_1$–$C_{12}$ alkyl, and each R is the same or different and is independently selected from hydrogen, optionally substituted alkyl, optionally substituted aryl or

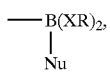

represents a cyclic group of the formula

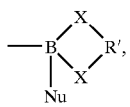

where X and Nu are as defined above and R' is optionally substituted alkylene, optionally substituted arylene or other divalent group consisting of aliphatic moieties linked to aromatic moieties;

with an organic compound having at a coupling position a halogen substituent or other substituent which undergoes substitution with the penta- or hexa-substituted diboron compound of formula (i) and/or formula (ii) in the presence of a Group VIII metal catalyst, such that a direct carbon to boron bond is formed between said coupling position and a boron-containing residue of the penta- or hexa-substituted diboron compound of formula (i) and/or formula (ii).

2. A process for the preparation of an organic boronic acid ester, organic boronic thioester or organic boronic acid amide comprising: (A) reacting a tetra-substituted diboron compound of formula

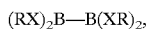

where R is hydrogen, optionally substituted alkyl or optionally substituted aryl or —$B(XR)_2$ represents a cyclic group of formula

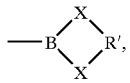

where each X, which is the same or different, is O, $S(O)_n$ where n is 1 or 2 or NR" where R" is hydrogen or $C_1$–$C_{12}$ alkyl, R' is optionally substituted alkylene, optionally substituted arylene or other divalent group consisting of aliphatic moieties linked to aromatic moieties; with a nucleophile to form a penta- or hexa-substituted diboron compound of formula (i) or (ii)

(i)

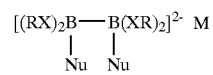

(ii)

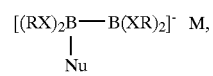

or a mixture of diboron compounds of formula (i) and (ii), wherein M is a counterion and Nu is a nucleophile, and each X, which is the same or different, is O, $S(O)_n$, where n is 1 or 2 or NR" where R" is hydrogen or $C_1$–$C_{12}$ alkyl, and each R is the same or different and is independently selected from hydrogen, optionally substituted alkyl, optionally substituted aryl or

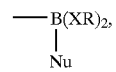

represents a cyclic group of the formula

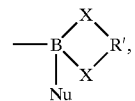

where X and Nu are as defined above and R' is optionally substituted alkylene, optionally substituted arylene or other divalent group consisting of aliphatic moieties linked to aromatic moieties;

(B) reacting the penta- or hexa-substituted diboron compound of formula (i) or (ii) or mixture of diboronic compounds of formula (i) and (ii) with an organic compound having at a coupling position a halogen substituent or other substituent which undergoes substitution with the penta- or hexa-substituted diboron compound of formula (i) and/or (ii) in the presence of a Group VIII metal catalyst such that a direct carbon to boron bond is formed between said coupling position and a boron containing residue of the penta- or hexa-substituted diboron compound of formula (i) and/or (ii).

3. A process for the preparation of an organic boronic acid ester, organic boronic thioester or organic boronic acid amide comprising:

(A) reacting a tetra-substituted diboron derivative of formula

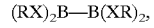

where R is hydrogen, optionally substituted alkyl or optionally substituted aryl or -$B(XR)_2$ represents a cyclic group of formula

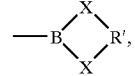

wherein each X, is the same or different, is O, $S(O)_n$ where n is 1 or 2 or NR" where R" is hydrogen or $C_1$–$C_{12}$ alkyl, R' is optionally substituted alkylene, optionally substituted arylene or other divalent group consisting of aliphatic moieties linked to aromatic moieties; with a nucleophile to form a penta- or hexa-substituted diboron compound of formula (i) or (ii)

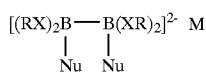 (i)

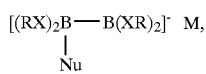 (ii)

or a mixture of diboron compounds of formula (i) and (ii), wherein M is a counterion and Nu is a nucleophile, and each X, which is the same or different, is O, $S(O)_n$, where n is 1 or 2 or NR" where R" is hydrogen or $C_1$–$C_{12}$ alkyl, and each R is the same or different and is independently selected from hydrogen, optionally substituted alkyl, optionally substituted aryl or

represents a cyclic group of the formula

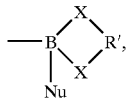

where X and Nu are as defined above and R' is optionally substituted alkylene, optionally substituted arylene or other divalent group consisting of aliphatic moieties linked to aromatic moieties;

(B) reacting said penta- or hexa-substituted diboron compound of formula (i) or (ii) or a mixture of diboron compounds of formula (i) and (ii) in situ with an organic compound having at a coupling position a halogen substituent or other substituent which undergoes substitution with the penta- or hexa-substituted diboron compound of formula (i) and/or (ii) in the presence of a Group VIII metal catalyst such that a direct carbon to boron bond is formed between said coupling position and a boron containing residue of the penta- or hexa-substituted diboron compound of formula (i) and/or (ii).

4. A process according to claim 1, wherein the organic compound is an aromatic ring compound.

5. A process according to claim 1, wherein the organic compound is an olefinic compound in which the halogen or other substituent which undergoes substitution with the penta- or hexa-substituted diboron compound of formula (i) and/or (ii) is in a vinylic coupling position.

6. A process according to claim 1, wherein the organic compound has a further substituents selected form the group consisting of hydroxy, amino, imino, acetylene, carboxy, carboxylato, carboximidyl, sulfo, sulfinyl, sulfinimidyl, sulfinohydroximyl, sulfonimidyl, sulfoniimidyl, sulfonohydroximyl, sulfamyl, phosphinyl, phosphinimidyl, phosphonyl, dihydroxyphosphanyl, hydroxyphosphanyl, phosphono, phosphonato, hydrohydroxyphosphoryl, allophanyl, guanidino, hydantoyl, ureido, and ureylene.

7. A process according to claim 1, wherein the organic compound has more than one halogen or other substituent which undergoes substitution with the penta- or hexa-substituted diboron compound of formula (i) and/or (ii).

8. A process according to claim 1, wherein the Group VIII metal catalyst is nickel, platinum, palladium or cobalt.

9. A process according to claim 8, wherein the catalyst is a palladium catalyst.

10. A process according to claim 9, wherein the catalyst is a palladium complex.

11. A process according to claim 2, wherein the tetra-substituted diboron compound is tetrahydroxydiboron, or an ester thereof.

12. A process according to claim 2, wherein the tetra-substituted diboron compound is selected from the group consisting of bis(pinacolato)diboron (the pinacol ester of diboronic acid), bis(ethanediolato)diboron, bis(n-propanediolato)diboron and bis(neopentanediolato)diboron.

13. A process according to claim 2, wherein the nucleophile is selected from the group consisting of hydroxide, alkoxide, phenoxide, alkylamino, amino, fluoride, cyano and thiolate.

14. A process according to claim 3, wherein the nucleotide is selected from the group consisting of hydroxide, alkoxide, phenoxide, alkylamino, amino, fluoride, cyano and thiolate.

15. A process according to claim 3, wherein the nucleophile is selected from the group consisting of methoxide, ethoxide, n-propoxide, i-propoxide, n-butoxide, t-butoxide, dimethylamino, diethylamino, diisopropylamino, fluoride, cyano and thiolate.

16. A process according to claim 14, wherein the nucleophile is selected from the group consisting of methoxide, ethoxide, n-propoxide, i-propoxide, -butoxide, t-butoxide, dimethylamino, diethylamino, diisopropylamino, fluoride, cyano and thiolate.

17. A process according to claim 13, wherein the nucleophile is a chiral nucleophile generated from (S)-(–)-1-phenylethanol; (R)-1-phenylethanol; (–)-1,2:5,6-Di-O-Isopropylidene-α-D-glycerol; (R)-(–)-1,2-O-Isopropylidene-glycerol; (+)-2,3-O-Isopropylidene-L-threitol; (–)-2,3-O-Isopropylidene-D-threitol; (S)-(+)-Methyl 3-hydroxy-2-methylpropionate; (S)-(R)-(–)-Methyl lactate; (R)-(–)-Methyl 3-hydroxy-2-methylpropionate; (S)-(+)-1-Amino-2-propanol; (R)-(–)-1-Amino-2-propanol; (+)-2,3-O-Isopropylidene-1,1,4,4-tetraphenyl-D-threitol; or (–)-2,3-L-Isopropylidene-1,1,4,4-tetraphenyl-L-threitol.

18. A process according to claim 14, wherein the nucleophile is a chiral nucleophile generated from (S)-(–)-1-phenylethanol; (R)-(+)-1-phenylethanol; (–)-1,2:5,6-Di-O-isopropylidene-α-D-glucofuranose; (+)-1,2:5,6-Di-O-isopropylidene-D-mannitol; (S)-(+)-1,2-O-Isopropylidene-glycerol; (R)-(–)-1,2-O-Isopropylidene-glycerol; (+)-2,3-O-Isopropylidene-L-threitol; (–)-2,3-O-Isopropylidene-D-threitol; (S)-(+)-Methyl 3-hydroxy-2-methylpropionate; (S)-(–)-Methyl lactate; (R)-(–)-Methyl 3-hydroxy-2-methylpropionate; (S)-(+)-1-Amino-2-propanol; (R)-(–)-1-Amino-2-propanol; (+)-2,3-O-Isopropylidene-1,1,4,4-tetraphenyl-D-threitol; or (–)-2,3-L-Isopropylidene-1,1,4,4-tetraphenyl-L-threitol.

19. A process according to claim 1 conducted in the presence of a solvent and a crown ether or cyclam, wherein the counterion M is coordinated with the crown ether or cyclam to assist in solubilising the nucleophile in the solvent.

20. A process for the preparation of an organic boronic acid comprising preparing an organic boronic acid ester according to the process of claim 1 and subjecting the organic boronic acid ester to hydrogenolysis or hydrolysis.

* * * * *